US009476094B2

(12) United States Patent
Densham

(10) Patent No.: US 9,476,094 B2
(45) Date of Patent: Oct. 25, 2016

(54) POLYNUCLEOTIDE SEQUENCING METHOD

(75) Inventor: Daniel Henry Densham, Devon (GB)

(73) Assignee: GEN-PROBE INCORPORATED, San Diego, CA (US)

( * ) Notice: Subject to any disclaimer, the term of this patent is extended or adjusted under 35 U.S.C. 154(b) by 1922 days.

(21) Appl. No.: 10/478,036

(22) PCT Filed: May 20, 2002

(86) PCT No.: PCT/GB02/02345
§ 371 (c)(1),
(2), (4) Date: Nov. 17, 2003

(87) PCT Pub. No.: WO02/095070
PCT Pub. Date: Nov. 28, 2002

(65) Prior Publication Data
US 2004/0241678 A1 Dec. 2, 2004

(30) Foreign Application Priority Data

May 18, 2001 (GB) .................................. 0112238.1

(51) Int. Cl.
 C12Q 1/00 (2006.01)
 C12Q 1/68 (2006.01)
(52) U.S. Cl.
 CPC .................................. *C12Q 1/6869* (2013.01)
(58) Field of Classification Search
 CPC .......... C12Q 1/6869; C12Q 2565/632; C12Q 2533/101; C12Q 2521/543
 See application file for complete search history.

(56) References Cited

U.S. PATENT DOCUMENTS

| 5,783,389 | A | * | 7/1998 | Vo-Dinh ............................ 435/6 |
| 5,866,430 | A | * | 2/1999 | Grow ............................ 436/172 |
| 5,958,696 | A | | 9/1999 | Crute |
| 6,046,038 | A | * | 4/2000 | Nilsen ........................ 435/91.1 |
| 6,048,982 | A | * | 4/2000 | Waggoner ..................... 548/148 |
| 6,331,392 | B1 | | 12/2001 | Laing et al. |
| 6,908,736 | B1 | * | 6/2005 | Densham ........................... 435/6 |
| 7,008,766 | B1 | * | 3/2006 | Densham ........................... 435/6 |
| 7,604,963 | B2 | | 10/2009 | Densham |
| 7,608,397 | B2 | | 10/2009 | Densham |
| 2004/0241719 | A1 | * | 12/2004 | Densham ........................... 435/6 |
| 2005/0214849 | A1 | * | 9/2005 | Densham ........................... 435/6 |
| 2008/0014592 | A1 | | 1/2008 | Densham |
| 2009/0029383 | A1 | | 1/2009 | Densham |

FOREIGN PATENT DOCUMENTS

| EP | 0 740 156 A1 | | 10/1996 |
| GB | WO9905315 | * | 2/1999 |
| GB | WO0053805 | * | 9/2000 |
| WO | WO 95/06138 A1 | | 3/1995 |
| WO | WO 99/05315 A2 | | 2/1999 |
| WO | WO 99/44045 A1 | | 9/1999 |
| WO | WO 00/36152 A1 | | 6/2000 |
| WO | WO 00/53805 A1 | | 9/2000 |
| WO | WO 00/60114 A2 | | 10/2000 |
| WO | WO 00/70073 A1 | | 11/2000 |
| WO | WO01/06257 | * | 1/2001 ........................ 435/6 |
| WO | WO 01/16375 A2 | | 3/2001 |
| WO | WO 01/23459 A1 | | 4/2001 |
| WO | WO 01/25480 A2 | | 4/2001 |

OTHER PUBLICATIONS

Lemon et al, Science, 198, vol. 282, pp. 1516-1519.*
Taton, et al, Science, vol. 289, pp. 1757-1760.*
Truskey, et al, Journal of Cell Science, vol. 103, pp. 491-499.*
Campagnola, et al, Biophysical Journal, 1999, vol. 77, 3341-3349.*
Vo-Dinh (trends in analytical chemistry (1998) vol. 17, p. 557-582).*
Miragliotta ( Johns Hopkins APL Technical digest (1995) pp. 348-357).*
Haller ( J. Chem Phys (90) (2) p. 1237-1252).*
Miragliotta et al ( johns Hopkins APL Technical digest (1995) vol. 16, pp. 348-357).*
Wilson et al (J. Applied Physics (1980) vol. 22, p. 119-128).*
Angeluts et (Novel Lasers and Devices Basic Aspects (NLDA) 1999 pp. 20-22).*
Kim et al (Lasers in Surgery and Medicine (2000) vol. 27, pp. 329-335).*
Gauderon et al (Micron (2001) vol. 32, pp. 685-689).*
Rinuy et al Biophysical Journal (1999) vol. 77, pp. 3350-3355).*
Campagnola, P.J. et al. "High-resolution nonlinear optical imaging of live cells by second harmonic generation" *Biophysical J.*, 1999, pp. 3341-3349, vol. 77.
Ha, T. et al. "Probing the interaction between two single molecules: Fluorescence resonance energy transfer between a single donor and a single acceptor" *Proc. Natl. Acad. Sci. USA*, 1996, pp. 6264-6268, vol. 93.
Jenkins, R.H. et al. "A novel Raman spectrophotometric method for quantitative measurement of nucleoside triphosphate hydrolysis" *Biospectroscopy*, 1999, pp. 3-8, vol. 5.
Lemon, K.P. and Grossman, A.D. "Localization of bacterial DNA polymerase: Evidence for a factory model of replication" *Science*, 1998, pp. 1516-1519, vol. 282.
Lewis, A. et al. "Second-harmonic generation of biological interfaces: probing the membrane protein bacteriorhodopsin and imaging membrane potential around GFP molecules at specific sites in neuronal cells of *C. elegans*" *Chem. Physics*, 1999, pp. 133-144, vol. 245.
McGilp, J.F. "A review of optical second-harmonic and sum-frequency generation at surfaces and interfaces" *J. Physics D. Applied Physics*, 1996, pp. 1812-1821, vol. 29, No. 7.

(Continued)

*Primary Examiner* — Steven Pohnert
(74) *Attorney, Agent, or Firm* — Brian S. Sun

(57) ABSTRACT

The subject invention pertains to a method for determining the sequence of a polynucleotide comprising the steps of (i) contacting a polynucleotide processive enzyme immobilised in a fixed position, with a target polynucleotide under conditions sufficient to induce enzyme activity; (ii) detecting an effect consequent on the interaction of the enzyme and polynucleotide, wherein the effect is detected by measurement of a non-linear optical signal or a linear signal coupled to a non-linear signal.

17 Claims, 2 Drawing Sheets

(56) References Cited

OTHER PUBLICATIONS

Nie, S. and Emory, S.R. "Probing single molecules and single nanoparticles by surface-enhanced Raman scattering" *Science*, 1997, pp. 1102-1106, vol. 275.

Peleg, G. et al. "Nonlinear optical measurement of membrane potential around single molecules at selected cellular sites" *Proc. Natl. Acad. Sci. USA*, 1999, pp. 6700-6704, vol. 96.

Peleg, G. et al. "Gigantic optical non-linearities from nanoparticle-enhanced molecular probes with potential for selectively imaging the structure and physiology of nanometric regions in cellular systems" *Bioimaging*, 1996, pp. 215-224, vol. 4.

Puppels, G.J. et al. "Confocal Raman microspectroscopy in biology: applications and future developments" *Trends Analyt Chem.*, 1991, pp. 249-253, vol. 10, No. 8.

Schultz, S. et al. "Single-target molecule detection with nonbleaching multicolor optical immunolabels" *PNAS*, 2000, pp. 996-1001, vol. 97, No. 3.

\* cited by examiner

POLYNUCLEOTIDE SEQUENCING METHOD

This application is the U.S. national stage application of International patent application No. PCT/GB02/02345, filed May 20, 2002.

FIELD OF THE INVENTION

This invention relates to a method for determining the sequence of a polynucleotide.

BACKGROUND OF THE INVENTION

The ability to determine the sequence of a polynucleotide is of great scientific importance, as shown by the Human Genome Project in mapping the three billion bases of DNA encoded in the human genome.

The principle method in general use for large-scale DNA sequencing is the chain termination method. This method was first developed by Sanger and Coulson (Sanger et al., Proc. Natl. Acad. Sci. USA, 1977; 74: 5463-5467), and relies on the use of dideoxy derivatives of the four nucleoside triphosphates which are incorporated into the nascent polynucleotide chain in a polymerase reaction. Upon incorporation, the dideoxy derivatives terminate the polymerase reaction and the products are then separated by gel electrophoresis and analysed to reveal the position at which the particular dideoxy derivative was incorporated into the chain.

Although this method is widely used and produces reliable results, it is recognised that it is slow, labour-intensive and expensive.

Fluorescent labels have been used to identify nucleotide incorporation onto a growing nascent DNA molecule, using the polymerase reaction (see WO91/06678). However, these techniques have the disadvantage of increasing background interference from the fluorophores. As the DNA molecule grows, the background "noise" increases and the time required to detect each nucleotide incorporation needs to be increased. This severely restricts the use of the method for sequencing large polynucleotides. The most serious limitation of polynucleotide sequencing systems built around fluorescent dyes, however, is the problem of photobleaching.

Photobleaching is a well documented phenomenon in fluorescent dye systems and results from exposure of the dye to excitation wavelengths. All dye systems have an ability to absorb a limited number of photons before photobleaching occurs. Once photobleaching has occurred the fluorescent dye is no longer visible to the observer and hence, if conjugated to a molecule, this will not be detectable.

There is therefore a need for an improved method for determining the sequence of a polynucleotide, which significantly increases the rate and fragment size of the polynucleotide being sequenced and which preferably does not depend on fluorescently labelled nucleotides for detection. Further, the method should be capable of being carried out by an automated process, reducing the complexity and cost associated with existing methods.

SUMMARY OF THE INVENTION

The present invention is based on the realisation that a conformational and/or mass and/or energy distribution change in a polynucleotide processive enzyme, which occurs when an enzyme associates with and moves along a target polynucleotide, can be detected using non-linear optical imaging, including that based on second or third harmonic generation.

According to the present invention, a method for sequencing a polynucleotide comprises the steps of:

(i) contacting a polynucleotide processive enzyme, immobilised in a fixed position, with a target polynucleotide under conditions sufficient for enzyme activity; and (ii) detecting an effect consequent on the interaction of the enzyme and the polynucleotide, wherein the effect is detected by measurement of a non-linear optical signal or a linear signal coupled to a non-linear signal.

Numerous advantages are achieved with the present invention. Sequencing can be carried out with small amounts of polynucleotide, with the capability of sequencing single polynucleotide molecules, thereby eliminating the need for amplification prior to initiation of sequencing. Long sequence read lengths can be obtained and secondary structure considerations minimised. Obtaining long read lengths eliminates the need for extensive fragment reassembly using computation. Further, as the invention is not dependent upon the need for fluorescently-labelled nucleotides or any measurement of fluorescence, the limitation of read length at the single molecule level as a function of photobleaching or other unpredictable fluorescence effects, is circumvented. The present invention also permits long polynucleotide fragments to be read sequentially by the same enzyme system. This has the benefit of allowing a single enzyme system to be used which can be regenerated and re-used allowing many different polynucleotide templates to be sequenced. Finally, the utilisation of Second or Third Harmonic Generation offers advantages due to the lack of photodamage and photobleaching. This is due to the fact that no photochemistry occurs, even in the focal plane because the signal, stimulated by non-resonant radiation, does not involve an excited state with a finite lifetime.

According to a second aspect of the invention, a solid support material comprises at least one polymerase and at least one dipolar molecule positioned on or proximal to the polymerase.

According to a third aspect of the invention, an imaging system set up to detect a non-linear optical signal, comprises a solid support having immobilised thereon an enzyme that interacts with a polynucleotide, and a dipolar molecule positioned on or proximal to the enzyme.

DESCRIPTION OF THE DRAWINGS

The invention is described with reference to the accompanying figure, wherein.

DETAILED DESCRIPTION OF THE INVENTION

Figure 1:
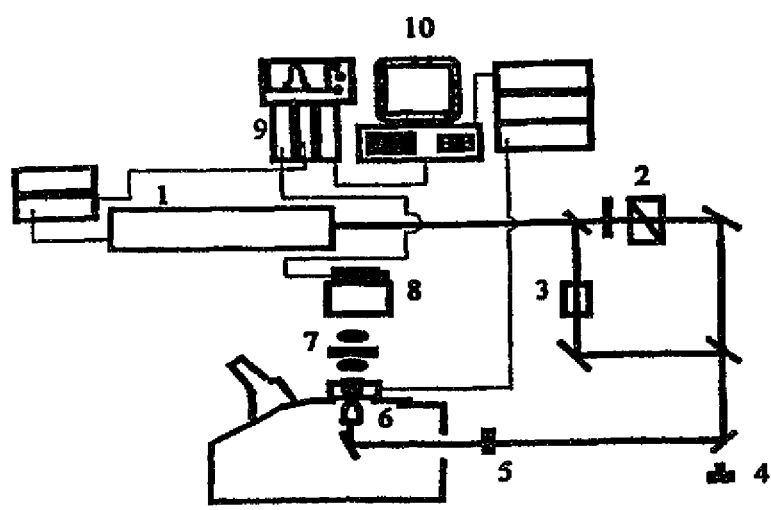
FIG. 1 is a schematic illustration of an imaging system that utilises second harmonic generation.

The present invention makes use of conventional non-linear optical measurements to identify a conformational and/or mass and/or energy distribution change occurring as a polynucleotide processive enzyme interacts with the individual bases on a target polynucleotide or incorporates nucleotides onto a nascent polynucleotide molecule.

The use of non-linear optical methods for imaging molecules is known. What has not been appreciated is that these methods can be applied to the sequencing of a polynucleotide, making use of an immobilised or fixed enzyme.

In a separate embodiment, a linear signal is generated in addition to a non-linear signal and the linear signal is detected. The two signals are said to be coupled, resulting in enhanced detection.

The term "polynucleotide" as used herein is to be interpreted broadly, and includes DNA and RNA, including modified DNA and RNA, DNA/RNA hybrids, as well as other hybridising nucleic acid-like molecules, e.g. peptide nucleic acid (PNA).

The term "polynucleotide processive enzyme" as used herein is to be interpreted broadly and relates to any enzyme that interacts with a polynucleotide and moves continuously along the polynucleotide. The enzyme is preferably a polymerase enzyme, and may be of any known type. For example, the polymerase may be any DNA-dependent DNA polymerase. If the target polynucleotide is a RNA molecule, then the polymerase may be a RNA-dependent DNA polymerase, i.e. reverse transcriptase, or a RNA-dependent RNA polymerase, i.e. RNA replicase. In a preferred embodiment of the invention, the polymerase is T4 polymerase. In further preferred embodiments of the invention, the polymerase is either E. coli polymerase III holoenzyme (McHenry, Ann. Rev. Biochem., 1988; 57:519); T7 polymerase (Schwager et al., Methods in Molecular and Cellular Biology, 1989/90; 1(4): 155-159) or bacteriophage T7 gene 5 polymerase complexed with E. coli Thioredoxin (Tabor et al., J. Biol. Chem., 1987; 262: 1612-1623). Each of these polymerase enzymes binds to a target polynucleotide with high processivity (and fidelity) and therefore maintains a polymerase-polynucleotide complex, even when polymerisation is not actively taking place.

Alternative enzymes that interact with a polynucleotide include helicase, primase, holoenzyme, topoisomerase or gyrase enzymes. Such enzymes offer further advantages. For example, using a helicase reduces the problem of secondary structures that exist within polynucleotide molecules, as helicases encounter and overcome these structures within their natural environment. Secondly, helicases allow the necessary reactions to be carried out on double-stranded DNA at room temperature.

As the enzyme interacts with successive bases on the polynucleotide, its conformation will change depending on which base (or nucleotide) on the target it is brought into contact with. Thus, the temporal order of base pair additions during the reaction is measured on a single molecule of nucleic acid, i.e. the activity of the enzyme system on the template polynucleotide to be sequenced can be followed in real time. The sequence is deduced by identifying which base (nucleotide) is being incorporated into the growing complementary strand of the target polynucleotide via the catalytic activity of the enzyme.

An important aspect of the present invention is the immobilisation of the enzyme in a fixed position relative to the imaging system. This is preferably carried out by immobilising the enzyme to a solid support, with the enzyme retaining its biological activity. Methods for the immobilisation of suitable enzymes to a solid support are known. For example, WO-A-99/05315 describes the immobilisation of a polymerase enzyme to a solid support. General methods for immobilising proteins to supports are suitable.

The optical detection methods used in the present invention are intended to image at the single molecule level, i.e. to generate a distinct image/signal for one enzyme. A plurality of enzymes may be immobilised on a solid support at a density that permits single enzyme resolution. Therefore, in one embodiment, there are multiple enzymes immobilised on a solid support, and the method of the invention can be carried out on these simultaneously. This allows different polynucleotide molecules to be sequenced together.

It will be apparent to the skilled person to carry out the imaging method under conditions suitable to promote enzymic activity. For example, with regard to a polymerase enzyme, it will be apparent that the other components necessary for the polymerase reaction to proceed, are required. In this embodiment, a polynucleotide primer molecule and each of the nucleoside triphosphates dATP, dTTP, dCTP and dGTP, will be required. The nucleoside triphosphates may be added sequentially, with removal of non-bound nucleotides prior to the introduction of the next nucleoside triphosphate. Alternatively, all the triphosphates can be present at the same time. It may be preferable to utilise triphosphates that have one or more blocking groups which can be removed selectively by pulsed monochromatic light, thereby preventing non-controlled incorporation. Suitable blocked triphosphates are disclosed in WO-A-99/05315.

High-resolution non-linear optical imaging systems are known in the art. In general, the non-linear polarisation for a material can be expressed as:

$$P = X^{(1)}E^1 + X^{(2)}E^2 + X^{(3)}E^3 + $$

where P is the induced polarisation, $X^{(n)}$ is the nth-order non-linear susceptibility, and E is the electric field vector. The first term describes normal absorption and reflection of light; the second describes second harmonic generation (SHG), sum and difference frequency generation; and the third describes light scattering, stimulated Raman processes, third harmonic generation (TGH), and both two- and three-photon absorption.

A preferred imaging system of the present invention relies on the detection of the signal arising from second or third harmonic generation.

Single-molecule resolution using second or third harmonic generation (hereinafter referred to as SHG) is known in the art (Peleg et al., Proc. Natl. Acad. Sci. USA, 1999; 95: 6700-6704 and Peleg et al., Bioimaging, 1996; 4:215-224).

The general set-up of the imaging system can be as described in Peleg et al., 1996, supra, and as shown in FIG. 1. With reference to FIG. 1, a laser (1) is used as the illumination source, to generate a laser beam which is then passed through a polarizer (2). Part of the laser beam may be directed through a non-linear crystal (3) to produce a green beam to aid the alignment of the laser beam. A photodiode (4) is placed in close proximity to the optical path in order to provide a means to monitor the generated near-infrared (NIR) intensity. A filter (5) is positioned in front of the entrance port of a microscope to prevent any second harmonic from entering the microscope. The laser beam is focussed onto the solid support comprising the immobilised enzyme, and the non-linear signal is collected by lenses (7) and detected using a monochromator (8). The fundamental intensity is blocked using an IR filter. The signal from the photomultiplier is amplified, averaged and integrated using a boxcar averager and channel integrator (9). The generated signals are then transferred to a computer (10) to generate the images.

In order to generate the second or third harmonic, it is necessary to position an appropriate label on or in close proximity to the immobilised enzyme. Highly dipolar molecules are suitable for this purpose. (Lewis et al. Chem. Phys., 1999; 245: 133-144). An example of suitable molecules are dyes, particularly styryl dyes (such as membrane dye JPW 1259—supplied by Molecular Probes). Green Fluorescent Protein (GFP) is another example of a "dye" or "label" which can be used to image via SHG. As used herein, GFP refers to both the wild-type protein, and spectrally shifted mutants thereof (Tsien, Ann. Rev. Biochem., 1998; 67:509 and U.S. Pat. Nos. 5,777,079 and 5,625,048). Other suitable dyes include di-4-ANEPPS, di-8-ANEPPS and JPW2080 (Molecular Probes).

The dipolar molecules may be located on the individual bases of the polynucleotide (or its complement if the dipolar molecules are attached to the nucleoside triphosphates and used in a polymerase reaction).

In a preferred embodiment of the invention, the enzyme, e.g. a polymerase, is prepared as a recombinant fusion with GFP. The GFP can be located at the N- or C-terminus of the enzyme (the C-terminus may be desirable if a polymerase is to be used in conjunction with a 'sliding clamp'). Alternatively, the GFP molecule can be located anywhere within the enzyme, provided that enzymic activity is retained.

In a separate embodiment of the present invention, the non-linear optical imaging system is Raman spectroscopy or surface enhanced Raman spectroscopy (SERS). An overview of Raman spectroscopy is contained in McGilp, Progress in Surface Science, 1995; 49(1):1-106.

The optical radiation used to excite the Raman system is, preferably, Near Infrared Radiation (NIR). NIR excitation has the advantage of decreasing the fluorescence and Raman signal of the surrounding medium or solvent.

In a separate embodiment of the invention, the non-linear signal can be enhanced by the use of a metal nanoparticle and/or a roughened metal surface (Boyed et al., Phys Rev., 1984; B. 30: 519-526, Chen et al., Phys. Rev. Lett., 1981; 46:1010-1012 and Peleg et al., 1996, supra). A signal enhancing metal nanoparticle can be conjugated to the enzyme (e.g. with a nanoparticle conjugated antibody, Lewis et al., Proc. Natl. Acad. Sci. USA, 1999; 96: 6700-6704), immobilised near the immobilised/localised enzyme or brought into close proximity to the SHG dye/enzyme.

A metal nanoparticle enhances the spectroscopic imaging associated with, in particular, SHG from nanometric regions, thereby permitting improved imaging at the single molecule level. Spectroscopic imaging based on Raman scattering can also be improved using a metal nanoparticle. Suitable metal nanoparticles are known, and include gold and silver nanoparticles. The nanoparticles are generally of a diameter of from 5 nm to 100 nm, preferably from 10 nm to 60 nm. The nanoparticles can be attached to the polynucleotide (or its complement if the nanoparticles are attached to nucleoside triphosphates and used in a polymerase reaction).

A roughened metal surface has also been shown to improve the sensitivity of the SHG process (Chen et al., 1981, supra and Peleg et al., 1996, supra) and is also a requirement for SERS. The metal surface is usually silver or another nobel metal. An initial selective modification of the metal surface at sub-wavelength spatial resolution can be carried out using various techniques, including the use of atomic force microscopy (AFM). A platinum-coated AFM tip can be used to catalyse hydrogenation of terminal azides to amino groups that are amenable to further derivatisation (Muller et al., Science, 1995; 268: 272-273). The enzymes can then be placed into "hot spots" where high local fields exist in regions where optical modes are localised (Shalaev et al. Phys. Rep., 1996; 272:61).

In a separate embodiment of the invention, a nanoparticle can be brought into close proximity with the enzyme using an AFM cantilever tip/probe, to thereby enhance the non-linear signal.

AFM has been shown recently to be capable of having a time resolution and sensitivity applicable to the dynamic imaging of protein conformational changes (Rousso et al., J. Struc. Biol., 1997; 119: 158-164). This is utilised in a preferred embodiment of the invention, where an AFM probe/tip is positioned over the enzyme and, in combination with non-linear optical information (e.g. SHG), used to detect conformational changes of a protein due to the interaction between the enzyme and the nucleotide sequence as the enzyme moves along the target polynucleotide. The information may be collected in the far-field using conventional confocal optics or in reflection mode if used in conjunction with total internal reflection.

In a further embodiment, the non-linear signal (e.g. SHG) is monitored in the near-field using Near-Field Scanning Optical Microscopy (NSOM). NSOM is a form of scanning probe microscopy, which makes use of the optical interaction between a nanoscopic tip (as used in AFM) and a sample to obtain spatially resolved optical information. Near-field microscopy in combination with SHG has been studied extensively and shown to be surface sensitive on an atomic scale (McGilp, 1995, supra). The main advantage of using NSOM as part of the imaging system is that it allows a large increase in resolution to sub-wave-length dimensions. As the present invention relates to the conformational monitoring of a single enzyme, e.g. a polymerase enzyme, as it interacts with a polynucleotide, sub-wave-length spatial resolution is highly desirable. In the context of this aspect of the invention, it is preferable if an AFM cantilever tip is used as an apertureless Near-field scanning microscope (Sangohdar et al, J. Opt. A: Pure Appl. Opt., 1999; 523-530). This is analogous to the use of metallic nanoparticles as a source of local field enhancement. It is preferred that the tip is made out of, or coated with, a nobel metal or any material which acts to increase the local electromagnetic field. Alternatively, a metallic nanoparticle may be connected directly to the cantilever tip. This has already been shown to be applicable to the monitoring of conformational changes at the single molecule level (Rousso, et al. supra).

In a further separate embodiment of the present invention, an independently generated surface plasmon (or polariton)/evanescent field can be used to enhance the signal-to-noise ratio of the non-linear signal. This evanescent wave enhanced imaging technique has greater signal-to-noise ratio than, for example, SHG imaging alone. In this embodiment, the evanescently enhanced SHG field signal from the labelled enzyme can be collected in the near field by an NSOM fibre whilst simultaneously obtaining AFM conformational data, and at the same time the amount of absorbed evanescent radiation can be monitored to obtain information on the amount of coupling between the evanescent field and the labelled polymerase/SHG field.

In this configuration (NSOM collection mode) the system acts as a photon scanning tunnelling microscope (PSTM) and the evanescent or surface plasmon field is coupled into the NSOM fibre probe tip. Any attenuation in the field strength of the signal reaching the tip by the polymerase will be monitored via a detector positioned at the end of the tip.

Surface plasmon resonance is known in the art, and relies on the generation of an evanescent wave by applying an incident light beam to a prism. A typical set-up for use in this embodiment consists of a prism which is coupled optically to a metal coated glass coverslip on which an enzyme is immobilised. The coverslip is part of a microfluidic flow cell system with an inlet for introducing ligands (nucleotides) over the immobilised enzyme. The enzyme is also labelled to allow non-linear effects to be generated. An incident light beam is applied to the prism to generate the surface plasmon field. At the same time, a non-linear signal (e.g. second harmonic field) is generated by directing a pulsed near infrared laser through a polarizer and half wave plate, into an optical scanner for beam control via a filter to eliminate optical second harmonic noise, and then into the sample. The non-linear optical signal is collected with lenses and a filter and directed into a monochromator, passed to a photomultiplier tube for detection and then amplified and recorded via a computer system.

When the non-linear optical is coupled to that generating the evanescent field, the signal that is detected can also be the linear (evanescent) signal. In this embodiment, the NSOM can be used in the collection made to detect the linear signal.

In a separate aspect of the present invention, the polynucleotide sequencing can be carried out within a cell.

It has been demonstrated that, in its native cellular environment, a DNA polymerase and its associated replisome complex is anchored in place (or localised in space) within the cell (Newport et al., Curr. Opin. Cell Biol., 1996; 8: 365; and Lemon et al., Science, 1998; 282: 1516-1519. This native anchored replication complex is analogous to the immobilisation of the enzyme to a solid support.

This allows the in vivo monitoring of conformational and template sequence-related changes of replisome-related molecules at the single molecule level to be carried out in real-time during DNA replication and/or cell division.

In order to carry out this aspect, it is necessary to modify the enzyme so that it can be imaged using nonlinear optical detection techniques. This can be achieved by genetic fusion of the enzyme with, for example, green fluorescent protein (GFP). The cell should also be immobilised to permit detection to occur.

The expressed fusion protein can be monitored/detected at its anchored cellular location via the application of non-linear optical detection (second harmonic generation).

The following Example illustrates the invention.

In this experiment, a fusion protein of Green Fluorescent Protein (GFP) and a polymerase was created via recombinant techniques well known in the art.

Quartz chips (14 mm in diameter, 0.3 mm thick) were spin-coated with a 50 nm thick layer of gold and then coated with a layer of planar dextran. These gold coated quartz chips were then placed into the fluid cell of a custom built Nearfield Scanning Optical Microscope (NSOM). The gold-coated quartz chips were coupled optically to a quartz prism via index matching oil. The fluid cell was then sealed and polymerase buffer was then allowed to flow over the chip.

Immobilisation of the polymerase to the chip surface was carried out according to Jonsson et al., Biotechniques, 1991; 11:620-627. The chip environment was equilibrated with running buffer (10 mM hepes, 10 mM MgCl$_2$ 150 mM NaCl, 0.05% surfactant P20, pH 7.4). Equal volumes of N-hydroxysuccinimide (0.1 M in water) and N-ethyl-N'-(dimethylaminpropyl) carbodimide (EDC) (0.1 M in water) were mixed together and injected across the chip surface, to activate the carboxymethylated dextran. The polymerase-GFP fusion protein (150 µl) was mixed with 10 mM sodium acetate (100 µl, pH 5) and injected across the activated surface. Finally, residual N-hydroxysuccinimide esters on the chip surface were reacted with ethanolamine (35 µl, 1 M in water, pH 8.5), and non-bound polymerase was washed from the surface. The immobilization procedure was performed with a continuous flow of running buffer (5 µl/min) at a temperature of 25° C.

50 µl of antibody binding buffer (10 mM MES pH 6.0, 150 mM NaCl, 3 mM EDTA) was flowed over the immobilized polymerase/GFP on the chip surface at a flow rate of 5 µl/min at 25° C. A primary antibody (GFP (B-2)B biotin conjugated 200 µl ml-1 Santa Cruz Biotechnology) was diluted 1:3000 in antibody binding buffer and allowed to flow over the chip surface at a flow rate of 5 µl/min for 30 minutes. Excess antibody was then washed off the surface by flowing antibody binding buffer over the chip at a flow rate of 5 µl/min for 30 minutes.

A secondary antibody (Immunogold conjugate EM Goat antimouse IgG (H+L) 40 nm, British Biocell International) was diluted 1:1000 in antibody binding buffer and allowed to flow over the chip surface at a flow rate of 5 µl/min for 30 minutes. Excess antibody was then washed off the surface by flowing antibody binding buffer over the chip at a flow rate of 5 µl/min for 30 minutes. The buffer was then returned to running buffer which was then allowed to flow over the chip at a rate of 5 µl/min for 30 minutes before initiation of the next stage.

Two oligonucleotides were synthesized using standard phosphoramidite chemistry. The oligonucleotide defined as SEQ ID NO. 1 was used as the target polynucleotide, and the oligonucleotide defined as SEQ ID NO. 2 was used as the primer.

```
CAAGGAGAGGACGCTGCTTGTCGAAGGTAAGGAACGG    SEQ ID NO. 1
ACGAGAGAAGGGAGAG

CTCTCCCTTCTCTCGTC                        SEQ ID NO. 2
```

The two oligonucleotides were reacted under hybridizing conditions to form the target-primer complex. The primed DNA was then suspended in buffer (20 mM Tris-HCl, pH 7.5, 8 mM MgCl$_2$, 4% (v/v) glycerol, 5 mM dithiothreitol (DDT) containing 150 µl of the β sub-units that form a sliding-clamp complex around the primer DNA. This process is known as pre-initiation.

In order to detect the conformational changes in the polymerase, a modified NSOM was used in tapping mode, with pulled quartz multimode 100 µm long fibre cantilevers. The cantilever was driven close to its resonant frequency and an initial area scan was carried out over the surface of the chip containing immobilized antibodies. The second harmonic signal was generated from the immobilized polymerase in the flow cell via initial illumination from a pulsed Near infra-red laser source. The NSOM tip was then scanned over the chip surface in the flow cell in order to obtain an image of a 40 nm gold particles in the flow cell which is associated with the polymerase. The tip is then held in stationary mode over the polymerase.

The pre-initiated pre-primed complex was then injected into the flow cell at a flow rate of 5 µl/min so that the "clamp" around the primer-template molecule forms a complex with the immobilized polymerase. The flow cell was maintained at 25° C. by a cooling device built into the flow cell.

The running buffer was then flushed continuously through the flowcell at 500 µl/min. After 10 minutes the sequencing reaction was initiated by injection of 0.4 mM dATP (8 µl) into the buffer at a flow rate of 500 µl/min. After 4 minutes 0.4 mM dTTP (8 µl) was injected into the flowcell. Then after another 4 minutes 0.4 mM dGTP (8 µl) was injected and after another 4 minutes 0.4 mM dCTP (8 µl) was injected. This cycle was then repeated 10 times. Over the entire time period the second harmonic signal transmitted via the multimode fibre was passed into a monochromator and then into a photomultiplier. The signal from the photomultipler was then amplified and fed into a computer for processing and storage.

The intensity change of second harmonic signal arising from the polymerase complex for a period of 10 seconds from the start of each injection was then calculated and plotted against nucleotide injected into the flow cell.

Figure 2:
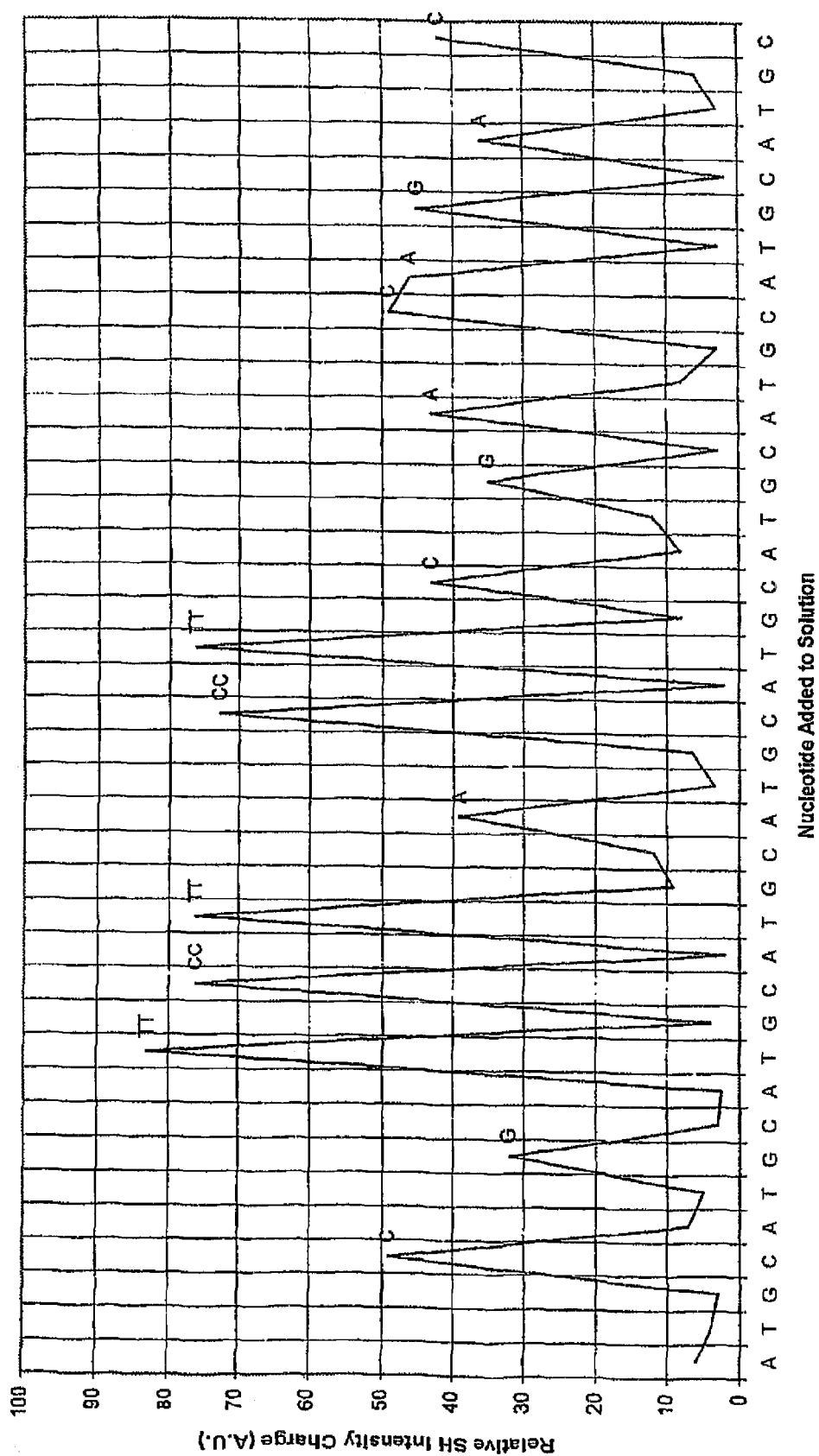
FIG. 2 shows the second harmonic signal generated by a polymerase on incorporation of a specific polynucleotide (SEQ ID NO:3).

The results of the sequencing reaction are shown in FIG. 2. As can be seen from the graph, large intensity changes (larger intensity changes accounting for identical nucleotides adjacent to each other) correspond to the complement of that of SEQ ID NO. 1 (reading from right to left, minus that part of which hybridizes to the primer sequence).

optical signal measurement consists of measuring the second or third harmonic signals, thereby determining the sequence of the polynucleotide.

2. The method according to claim 1, wherein the enzyme is a polymerase.

3. The method according to claim 1, wherein the enzyme is a helicase or primase enzyme.

4. The method according to claim 1, wherein the nanoparticle is a gold or silver nanoparticle.

5. The method according to claim 1, wherein there are a plurality of enzymes immobilised on the solid support.

6. The method according to claim 1, wherein the solid support has a roughened metal surface.

The invention claimed is:

1. A method for determining the sequence of a polynucleotide, consisting essentially of the sequential steps of:
   (i) contacting a polynucleotide processive enzyme immobilised in a fixed position having a metal nanoparticle positioned on or proximal to the enzyme with a target polynucleotide to form a complex;
   (ii) contacting the complex with one or more nucleoside triphosphates selected from the group consisting of dATP, dTTP, dGTP, and dCTP, under conditions sufficient to induce polynucleotide processive enzyme activity;
   (iii) generating a non-linear optical signal in the area encompassing at least a portion of the immobilized enzyme; and
   (iv) detecting an effect as the complex interacts with the one or more nucleoside triphosphates, by measurement of the non-linear optical signal, wherein the non-linear 7. The method according to claim 1, further comprising the application of localised surface plasmon resonance.

8. The method according to claim 5, wherein the solid support has a roughened metal surface.

9. The method according to claim 5, wherein the support is silver or gold.

10. The method of claim 1 further comprising immobilizing the polynucleotide processive enzyme on a solid support prior to contacting the enzyme with a target polynucleotide.

11. The method of claim 1, wherein steps (ii)-(iv) are repeated utilizing the same complex.

12. A method for determining the sequence of a polynucleotide, comprising the sequential steps of:
   (i) contacting a polynucleotide processive enzyme immobilised in a fixed position having a metal nanoparticle positioned on or proximal to the enzyme with a target polynucleotide to form a complex;

(ii) contacting the complex with one or more nucleoside triphosphates selected from the group consisting of dATP, dTTP, dGTP, and dCTP, under conditions sufficient to induce polynucleotide processive enzyme activity;

(iii) generating a surface plasmon/evanescent field in an area encompassing at least a portion of the immobilized enzyme;

(iv) generating a non-linear optical signal in the area encompassing at least a portion of the immobilized enzyme, wherein the non-linear imaging signal is generated utilizing a near infrared laser, and wherein the non-linear optical signal is coupled to the surface plasmon/evanescent field signal such that the surface plasmon/evanescent field enhances the signal-to-noise ratio of the non-linear signal; and (v) detecting an effect as the complex interacts with the one or more nucleoside triphosphates, thereby determining the sequence of the polynucleotide, wherein the effect is detected by measurement of the non-linear signal, and wherein the non-linear optical detection is second or third harmonic generation imaging.

13. The method of claim 12, wherein the effect detected is a change in conformation of the enzyme.

14. The method of claim 12, wherein the surface plasmon/evanescent field signal is monitored to analyze the coupling of the non-linear field with the plasmon/evanescent field.

15. The method according to claim 12, wherein there are a plurality of enzymes immobilised on the solid support.

16. The method of claim 12 further comprising immobilizing the polynucleotide processive enzyme on a solid support prior to contacting the enzyme with a target polynucleotide.

17. The method of claim 12, wherein steps (ii)-(v) are repeated utilizing the same complex.

* * * * *

SEQUENCE LISTING

```
<160> NUMBER OF SEQ ID NOS: 3

<210> SEQ ID NO 1
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 1
caaggagagg acgctgcttg tcgaaggtaa ggaacggacg agagaaggga gag            53

<210> SEQ ID NO 2
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 2
ctctcccttc tctcgtc                                                   17

<210> SEQ ID NO 3
<211> LENGTH: 21
<212> TYPE: DNA
<213> ORGANISM: Artificial Sequence
<220> FEATURE:
<223> OTHER INFORMATION: polynucleotide sequence

<400> SEQUENCE: 3
cgttccttac cttcgacaga c                                              21
```